(12) United States Patent
Vann et al.

(10) Patent No.: US 6,192,884 B1
(45) Date of Patent: Feb. 27, 2001

(54) METHOD AND APPARATUS FOR SUPPLEMENTAL OXYGEN DELIVERY

(75) Inventors: Richard D. Vann, Durham, NC (US); Stephen R. Muza, Jr., Medway, MA (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/083,811

(22) Filed: May 22, 1998

(51) Int. Cl.$^7$ ............................ A61M 16/00; A62B 7/04; F16K 31/26
(52) U.S. Cl. ...................... 128/204.26; 128/205.24; 128/205.25; 128/206.21; 128/206.28
(58) Field of Search .............. 128/204.18, 204.23, 128/204.26, 205.24, 205.25, 206.21, 206.28

(56) References Cited

U.S. PATENT DOCUMENTS

| | | | |
|---|---|---|---|
| 2,843,121 | 7/1958 | Hudson | 128/146 |
| 3,837,337 * | 9/1974 | LaViolette | 128/205.12 |
| 4,226,234 * | 10/1980 | Gunderson | 128/205.24 |
| 4,345,592 * | 8/1982 | Giorgini | 128/204.26 |
| 4,345,593 * | 8/1982 | Sullivan | 128/204.26 |
| 4,433,685 * | 2/1984 | Giorgini et al. | 128/204.26 |
| 4,458,679 * | 7/1984 | Ward | 128/201.13 |
| 4,612,928 * | 9/1986 | Tiep et al. | 128/204.23 |
| 4,665,911 * | 5/1987 | Williams et al. | 128/204.21 |
| 4,686,974 | 8/1987 | Sato et al. | 128/204.23 |
| 4,706,683 | 11/1987 | Chilton et al. | 128/654 |
| 4,932,402 * | 6/1990 | Snook et al. | 128/204.23 |
| 5,005,570 * | 4/1991 | Perkins | 128/204.23 |
| 5,024,219 * | 6/1991 | Dietz | 128/204.21 |
| 5,109,839 * | 5/1992 | Blasdell et al. | 128/203.12 |
| 5,241,955 | 9/1993 | Dearman et al. | 128/204.18 |
| 5,280,780 | 1/1994 | Abel | 128/203.14 |
| 5,311,862 * | 5/1994 | Blasdell et al. | 128/205.25 |
| 5,320,093 * | 6/1994 | Raemer | 128/203.12 |
| 5,348,000 * | 9/1994 | Teves | 128/204.18 |
| 5,503,146 * | 4/1996 | Froehlich et al. | 128/204.23 |
| 5,551,419 * | 9/1996 | Froehlich et al. | 128/204.23 |
| 5,558,086 * | 9/1996 | Smith et al. | 128/204.26 |
| 5,603,315 * | 2/1997 | Sasso, Jr. | 128/204.18 |
| 5,666,945 | 9/1997 | Davenport | 128/200.14 |
| 5,676,133 * | 10/1997 | Hickle et al. | 128/205.12 |
| 5,794,615 * | 8/1998 | Estes | 128/204.23 |
| 5,839,434 * | 11/1998 | Enterline | 128/204.23 |
| 5,865,174 * | 2/1999 | Kloeppel | 128/204.23 |
| 5,918,596 * | 7/1999 | Heinonen | 128/204.21 |
| 6,065,473 * | 5/2000 | McCombs et al. | 128/204.18 |

* cited by examiner

*Primary Examiner*—John G. Weiss
*Assistant Examiner*—Joseph F. Weiss, Jr.
(74) *Attorney, Agent, or Firm*—Jenkins & Wilson, P.A.

(57) ABSTRACT

An apparatus and method for supplemental oxygen administration to a patient that provides enhanced efficiency of oxygen use due to the administration of an oxygen bolus at the beginning of each inhalation by a patient. The supplemental oxygen delivery device utilizes first and second one-way valves corresponding to air inspiration and air expiration ports, respectively, and that are positioned in an air pathway so that air inspiration opens the first one-way valve to permit air flow through the air inspiration port and air expiration closes the first one-way valve and opens the second one-way valve to permit air expiration through the air expiration port. An oxygen supply source is connected to the device so as to provide an air bolus in the air pathway upstream and in front of the first one-way valve so as to provide a burst of oxygen during the first part of inhalation.

23 Claims, 17 Drawing Sheets

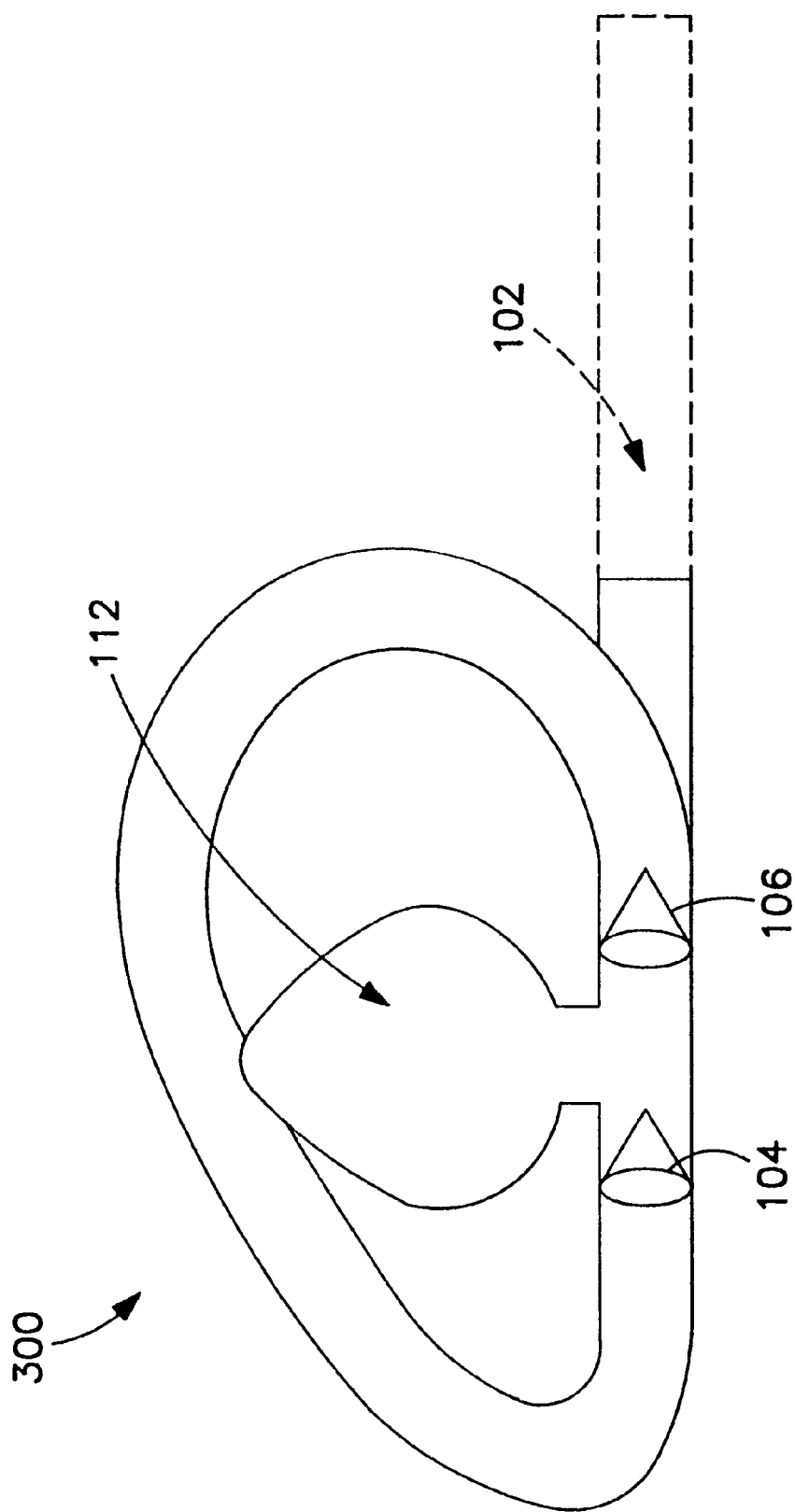

METHOD AND APPARATUS FOR SUPPLEMENTAL OXYGEN DELIVERY

TECHNICAL FIELD

The present invention relates to a device and method for providing supplemental oxygen to a living body during respiration. More particularly, the invention relates to an improved supplemental oxygen delivery device and method therefore that is simpler in construction and utilizes less oxygen to achieve a given oxygen level in breathing than devices and methods known heretofore.

BACKGROUND ART

Supplementary oxygen is of critical importance in many situations, including use (1) as a first aid measure, (2) treatment of chronically ill patients, and (3) prevention of hypoxemia (lack of oxygen in arterial blood) at high altitudes. The therapeutic effects of supplementary $O_2$ include: elimination of nitrogen bubbles in tissue or blood vessels, oxygenation of plasma to increase physically dissolved oxygen, reduction of tissue edema, and increase $O_2$ saturation of hemoglobin. In each of these examples, the user of a supplementary oxygen delivery system desires to maintain a certain inspired $O_2$ percentage for a given duration of time. However, in some situations such as in remote locations, the supply of available oxygen is limited. This makes the efficiency of the delivery system an important factor. Also, the percentage of oxygen required may differ according to the situation. For example, in many emergency applications as close to 100% inspired $O_2$ as possible is desired.

On the other hand, for high altitude applications, a percentage only high enough to achieve 90% arterial $O_2$ saturation may be sufficient. Therefore, control of the percentage of oxygen delivered to an individual is significant in making a system versatile as well as efficient. Applicants' invention provides a system with improved efficiency for delivering a given percentage of $O_2$ for the longest duration.

EMERGENCY APPLICATIONS OF SUPPLEMENTAL OXYGEN

In many emergency situations, paramedics will administer oxygen to a patient until he reaches a treatment center. Typically, oxygen is delivered via a nasal cannula or oro-nasal mask with a constant flow. This allows the patient to inhale about 40–50% $O_2$, depending on the flow from the oxygen tank. Often it is sufficient to increase the $O_2$ concentration only slightly, but in many situations, 100% $O_2$ or as close as possible is the most important treatment. Emergency Normobaric Oxygen Therapy (NBO) administers 100% $O_2$ at normal atmospheric pressure. NBO is indispensable in air embolism and decompression sickness from diving or altitude exposure, cardiac arrest/cardiovascular insufficiency, and carbon monoxide intoxication and smoke inhalation. It is important to begin with oxygen as soon as possible since delay can negatively affect the final outcome.

In diving accidents, gas bubbles composed primarily of nitrogen form in the blood or tissues. By eliminating all nitrogen in the lungs with 100% oxygen, the nitrogen gradient between the blood and tissues is increased and causes accelerated resolution of the bubbles. With carbon monoxide poisoning, the CO competes with and is 200 times more stable when bound to hemoglobin than is oxygen. Since the arterial $O_2$ tension of a person breathing 100% $O_2$ can approach 700 mmHg (as opposed to about 100 mmHg when breathing air), this elevated $O_2$ tension displaces CO from hemoglobin and replaces it with $O_2$ In emergencies such as these, oxygen administration as a first aid measure may be of critical importance.

The principle behind using supplemental oxygen as a first aid measure is to deliver the highest concentration possible until arrival at a medical center. The device most often used to accomplish this is a non-rebreathing mask attached to a reservoir bag (see FIG. 1). This device functions similarly to a demand regulator used in SCUBA. The oxygen supply flows constantly into the reservoir, and when the patient inhales, 100% $O_2$ is drawn from the reservoir through a non-return (one-way) valve. The flow must be high enough so that the reservoir bag is not completely deflated during inhalation. The patient then exhales the used $O_2$ to the atmosphere through a second one-way valve that prevents the inspiration of air. This system requires an $O_2$ flow rate equal to the breathing rate (minute ventilation), so it is very difficult to maintain a high $O_2$ percentage for very long without exhausting the $O_2$ supply. In situations such as diving accidents, the nearest treatment facility may be hours away, and the supply of oxygen may be very limited.

APPLICATION OF SUPPLEMENTAL OXYGEN FOR CHRONIC ILLNESS IN REMOTE AREAS

While sufficient environmental oxygen is present at normal atmospheric pressures, trauma or disease may interfere with oxygenation of the blood in the lungs or with the delivery of oxygenated blood by the heart and circulatory system. In such situations, it may be desirable to achieve an inspired $O_2$ fraction above the 20.9% in air. Chronically ill patients with poor gas exchange in the lungs due to pulmonary disease or poor blood circulation due to cardiovascular disease are often administered an elevated percentage of oxygen in order to raise the $O_2$ in their arterial blood nearer to normal. (The normal arterial oxygen tension in the blood is about 100 mmHg; however, for patients suffering from cardiopulmonary disease, this level may be difficult to achieve). A supplemental oxygen system with an adjustable flow is used in these cases to maintain the desired $O_2$ level in the blood. Administration of Normobaric Oxygen is without hazard for less than about 8 hours as used during immediate first aid. Exposure to 100% oxygen for longer periods, however, can cause chronic irritations known as pulmonary oxygen toxicity. The first noticeable signs of pulmonary toxicity are chest soreness and sore throat which occur after about 8 hours, but potentially serious damage does not occur until after about 48 hours. Patients may be treated with 40 to 50 percent oxygen for an extended duration since this percentage is low enough to avoid the danger of pulmonary oxygen toxicity.

In medical treatment centers with a virtually unlimited supply of oxygen, maintaining 40–50% oxygen is not difficult. However, for military casualties and patients who live in rural areas, the oxygen supply must be used more conservatively. Under these circumstances, an efficient $O_2$ delivery system is also required. Presently, a non-rebreathing mask without a reservoir (FIG. 2) is the most commonly used system. This system supplements air inspired from the atmosphere with a low but constant flow of oxygen, and one-way valves prevent rebreathing.

HIGH ALTITUDE APPLICATIONS OF SUPPLEMENTAL OXYGEN

For mountain climbers, aviators, and high altitude parachutists, supplemental oxygen is very important. At high altitudes, atmospheric pressure decreases causing the partial pressure of oxygen to decrease. Although the percentage of oxygen in the atmosphere is the same at high altitude as at sea level (the amount of oxygen in air is 20.93% up to 110 km), the reduced atmospheric pressure makes the air less dense, and a smaller mass of oxygen enters the lungs with each inhalation. The effect is equivalent to breathing a lower percentage of oxygen at sea level. This situation can result in a deficiency of oxygen in the blood, or hypoxemia. The symptoms of hypoxemia include heavy breathing, lightheadedness, euphoria, overconfidence, apathy, fatigue, visual disturbances, chest pain, unconsciousness, seizures, and even death. These symptoms become apparent when the arterial oxygen saturation drops below about 87% (arterial $O_2$ tension of about 55 mmHg), and below 65% (arterial $O_2$ tension of about 35 mmHg) the symptoms become severe and the subject may lose consciousness.

There are two types of high altitude exposure which require supplemental oxygen: aviation and mountaineering. Military combat aviators, for example, are susceptible to acute hypoxia when they ascend to altitude rapidly. Nonetheless, they must maintain their capabilities for judgment, decision making, and physical performance. Since an error in judgment can be deadly, no degree of hypoxia is tolerable. Combat aviators remain at high altitudes for only a few hours, however, unlike mountain climbers who may spend days to months at altitude.

Mountain climbers are exposed to chronic hypoxia which can cause Acute Mountain Sickness (AMS). Although the early manifestations of AMS are relatively benign, they may progress into malignant forms such as High Altitude Pulmonary or Cerebral Edema (HAPE or HACE). HAPE and HACE are caused by increased hydrostatic pressure in the capillaries, and edema fluid flooding into the alveoli (HAPE) or brain (HACE). For most lowlanders, symptoms of hypoxia do not occur until altitudes of greater than 3,000 meters (10,000 feet), but if ascent is slow, a climber can acclimatize at intermediate altitudes of up to 5,800 meters (19,000 feet). Above this altitude, short sojourns are possible, but the incidence of altitude sickness increases, and climbers often use $O_2$ above 25,000 feet.

When AMS occurs in a climber, it can often be cured by descending only a few thousand feet. Mild hypoxia is not as dangerous for a climber as it is for an aviator, and so most climbers tolerate the early symptoms. As the climber continues to ascend however, supplemental $O_2$ may be required to improve performance and reduce the symptoms. An individual who ignores the symptoms and continues to climb faces increasing hypoxia, and a potentially life threatening situation should HAPE or HACE develop. With HAPE or HACE, increased partial pressure of $O_2$ must be administered, and the climber must descend if he or she is to avoid death.

Hypoxia can be ameliorated by using supplemental oxygen, increasing the breathing rate (hyperventilation), or a combination of the two. Drugs such as acetazolamide are used to increase ventilation, but these drugs have side effects and are not fully effective for some people. Another effect of hypoxia is to stimulate hyperventilation which eliminates carbon dioxide and renders an individual hypocapnic. As $CO_2$ is both a ventilatory stimulant and a cerebral vasodilator that increases blood flow to the brain, hypoxic ventilatory drive can have undesirable side effects. Since the inhalation of $CO_2$ stimulates ventilation, supplemental $CO_2$ can be used as a method of increasing the $O_2$ levels in the blood. The drawback to this alternative is the risk of hypercarbia, or the presence of excessive amounts of $CO_2$ in the blood. Severe hypercarbia can cause heavy breathing, sweating, weakness, air hunger, clumsiness, dizziness, headache, depression, and unconsciousness.

The ideal method for reducing hypoxia would be to use supplementary oxygen to raise the percentage of oxygen enough so that the partial pressure is the same as at sea level (about 150 mm of Hg). However, climbers, parachutists, and pilots are limited in the amount of supplemental $O_2$ they can carry, so this is rarely achieved. A system which could increase oxygen delivery efficiency is desirable.

THE PHYSIOLOGY OF SUPPLEMENTAL OXYGEN DELIVERY

In a healthy, non-smoking person, about ⅓ of the breathing cycle is inhalation and ⅔ is exhalation. Only a fraction of inhaled air actually gets to the alveoli of the lungs where the $O_2$ is absorbed. The remainder is trapped in the trachea, bronchi, and upper airways where there is no gas exchange with the blood. The airways which extend from the lips down to the beginning of the alveoli constitute the anatomical deadspace.

Another form of deadspace is the result of ventilation-perfusion (V/Q) mismatch. V/Q mismatch means that one section of alveoli is underventilated while another section is underperfused. The result of ventilation-perfusion inequalities is functionally equivalent to anatomical deadspace. Since it is difficult to partition the overall deadspace into its anatomical and V/Q components, the term physiological deadspace is used to refer to the combined effects of anatomical deadspace and ventilation-perfusion inequality.

The ideal way to deliver oxygen to a subject would be to have the highest $O_2$ concentration enter the lungs first. Oxygen delivered at the beginning of the inhalation cycle travels deepest to the functional part of the lungs, the alveoli, allowing optimum absorption. The gas inhaled at the end of inspiration can be hypoxic since this gas occupies the anatomical deadspace and takes no part in respiratory exchange. The fraction of $O_2$ in the end-tidal exhalation most accurately reflects the amount of $O_2$ available for exchange in the lungs and is the focus of measurements reported below.

Another method for conserving supplemental oxygen is to rebreathe gas that never penetrates the lungs further than the anatomical deadspace (upper airways). Too much rebreathing can be counterproductive, however, if it includes more than a minimal volume of gas that has participated in respiratory exchange and is depleted of $O_2$ and rich in $CO_2$. On the other hand, $CO_2$ is a ventilatory stimulant and a cerebral vasodilator which may be beneficial at altitude to correct the hypocapnia that occurs in response to hypoxia-induced hyperventilation. Rebreathing would also act to conserve heat and moisture which could ameliorate the hypothermia and drying of the upper airways that can occur in mountain climbers. Reported below are measurements that show improved efficiency of oxygenation as a result of partial rebreathing of expired gas.

PRESENTLY KNOWN SYSTEMS FOR SUPPLEMENTAL $O_2$ DELIVERY

There are three principle methods for $O_2$ delivery: (1) open circuit (see FIGS. 1 and 3), (2) closed circuit (see FIG. 4), and (3) ambient air (see FIG. 2) with supplemental oxygen. In an open circuit device, the user inhales gas (100% $O_2$) directly from a supply tank or intermediate reservoir. The exhaled gas is then released to the atmosphere. The conventional demand regulator is an example of an open circuit system. This is the same device as used for SCUBA diving. An open circuit is the most certain method of delivering 100% $O_2$ to the user, but since the user can consume from 8 to 45 liters of $O_2$ per minute depending on workload, this method requires a very large supply of oxygen. The requirement for a large $O_2$ supply makes open circuit impractical for most remote applications and particularly in mountaineering where oxygen supplies must be person-carried.

A conventional closed circuit oxygen system (see FIG. 4) is composed of a breathing bag, a carbon dioxide scrubber, an oxygen supply, and connecting hoses. Oxygen is inhaled from the breathing bag, delivering 85–95% oxygen to the lungs. In the lungs, $O_2$ is absorbed and $CO_2$ is removed from the alveoli. The expired gas then enters a scrubber where $CO_2$ is removed, and the remaining $O_2$ is recirculated back to the breathing bag. Since the user consumes some of the oxygen, the volume in the breathing bag is now slightly less than before exhalation, and $O_2$ is added from an outside source to return the initial volume. The user then inhales from the bag again, and the cycle repeats. The circuit must be purged with additional oxygen to flush out nitrogen and achieve a high oxygen percent.

The biggest advantage of the closed circuit system is that the user can rebreathe the expired oxygen. A closed circuit system requires only a little more oxygen than the user consumes. A closed circuit is the most efficient way to maintain a high $O_2$ percentage in the lungs, and usually an $O_2$ flow rate of 0.5–2 liter per minute (1pm) is adequate. As long as the system works properly, hypoxia and hypercapnia cannot occur. There are a few shortcomings, however, as the duration of the system is limited not only by the $O_2$ supply, but also by the amount of $CO_2$ absorbent available. While several hundred grams of absorbent will last for hours, it is a consumable item that, like oxygen, must be replenished. If the closed circuit is used longer than the duration of the $CO_2$ absorbent, hypercapnia can occur. Therefore, extra $CO_2$ absorbent must be transported along with the breathing bag, hoses, and $O_2$ supply. Closed circuit oxygen is more expensive and complex than open circuit and requires additional training.

The conventional system used most commonly today for both emergency and high altitude applications is ambient air with supplemental oxygen (see FIG. 2). With this system, a constant flow of oxygen is inhaled simultaneously with air from the surrounding environment. Examples include the nasal cannula and the LAERDAL POCKET MASK™ made by Laerdal Medical Corporation of Armonk, New York. The fraction of inspired oxygen is regulated by the flow from the supply tank, and the expired gas is released to the atmosphere. The benefits of this system are that it uses smaller amounts of $O_2$ than open circuit, does not require a $CO_2$ scrubber, is relatively simple to use, and is lightweight and inexpensive. A disadvantage of the system is that it cannot effectively deliver 100% oxygen even at high flows although to prevent hypoxia at moderate altitudes, administering pure oxygen is not necessary. Another disadvantage is that oxygen is wasted since the $O_2$ flow continues during exhalation, but less oxygen is wasted than with open circuit supplemental oxygen delivery.

DISCLOSURE OF THE INVENTION

The present invention provides a supplemental oxygen delivery device that is synchronized to breathing and its related method of use. The device comprises breathing means adapted to communicate with the mouth or nose and mouth of the patient and defines an air pathway including an air inspiration port and an air expiration port. First and second one-way valve means are provided that correspond to the air inspiration port and the air expiration port, respectively, and that are positioned in the air pathways so that patient air inspiration opens the first valve means to permit air flow through the air inspiration port and patient air expiration closes the first valve means and opens the second valve means to permit expiration through the air expiration port. An oxygen supply source is fluidly connected with the breathing means and acts to provide a desirable oxygen bolus in the gas pathway upstream and in front of the first valve means. In this manner, a burst of oxygen is provided during the first portion of a patient's inhalation so as to minimize oxygen required to achieve a given oxygen level in a patient breathing from the supplemental oxygen device.

It is therefore an object of the present invention to provide an improved supplemental oxygen device that is simple in construction and minimizes the use of oxygen to achieve a desired oxygen level in a patient or other user.

It is another object of the present invention to provide an improved supplemental oxygen device that is adapted to provide a burst of oxygen during only the first part of inhalation to avoid loss of oxygen during exhalation.

It is another object of the present invention to provide an improved supplemental oxygen delivery device that provides a higher concentration of oxygen in the desirable early part of inhalation and that operates more efficiently with a given oxygen supply than conventional supplemental oxygen delivery devices.

It is still another object of the present invention to provide a supplemental oxygen delivery device that is at least twice as efficient as conventional and well known supplemental oxygen delivery devices.

Some of the objects of the invention having been stated hereinabove, other objects will become evident as the description proceeds, when taken in connection with the accompanying drawings as best described hereinbelow.

Additional objects include the partial rebreathing of exhaled deadspace gases to recapture oxygen (primarily) and heat, moisture, and carbon dioxide (secondarily) for certain applications.

BRIEF DESCRIPTION OF THE DRAWINGS

FIG. 8A shows the device of FIG. 8 in the form of an oro-nasal mask;

BEST MODE FOR CARRYING OUT THE INVENTION

As is well known to those of skill in the art, the gas that enters the nose, mouth, and upper airways at the end of inspiration is trapped in the anatomical deadspace where there is no gas exchange. This gas is discharged at the beginning of exhalation. The efficiency of oxygen delivery can be increased by rebreathing the unused gas. A class of devices known as Mapleson anesthesia circuits takes advantage of this principle to improve efficiency. This is the principle used in applicants' partial rebreather device.

A second method of improving oxygen efficiency is to add oxygen only at the very beginning of inspiration. This is the principle which applicants call "early oxygen addition". Applicants' implementations of early $O_2$ additions are improvements by being simpler and less costly. The OXYSAVER® cannula (made by Aerox Aviation Oxygen Systems of Stratford, Conn.), the PULSEDOSE® regulator (made by DeVilbiss Health Care, Inc. of Somerset, Pa.), and the EDS oxygen delivery system (made by Mountain High Equipment and Supply Company of Salt Lake City, Utah) are examples of devices which use this principle. The OXYSAVER® has a small reservoir under the nostrils in which a volume of oxygen collects while the user exhales. This oxygen is inspired at the start of each inhalation. The EDS system has a pressure transducer that senses the beginning of inspiration and injects a preset bolus of $O_2$ into an oro-nasal mask. This device is used to reduce hypoxia at high altitude, and the bolus volume can be adjusted for different altitudes. The PULSEDOSE® system works in a similar fashion to the EDS systems.

Figure 5:
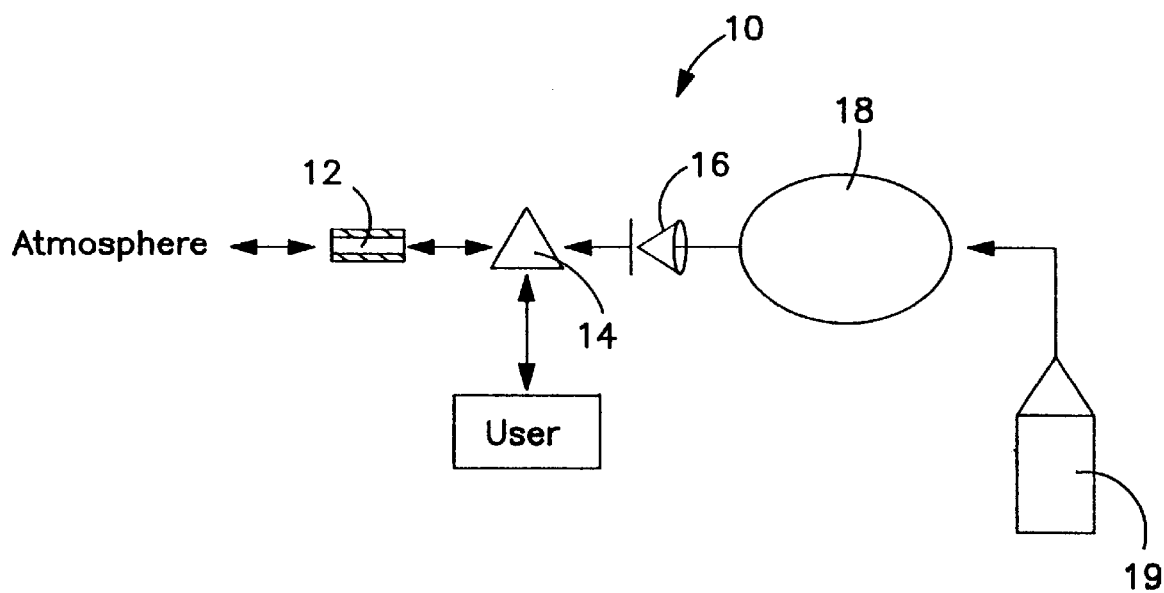
FIG. 5 is a schematic view of a well known prior art supplemental oxygen delivery system.

Applicants' invention is an improvement to supplemental oxygen delivery systems. The prior art device 10 of FIG. 5 tested a different implementation of the early addition principle for the prevention of hypoxemia in hypoxic environments. This device comprises non-sectional area reducer 12, mouthpiece 14, valve 16, reservoir bag 18 and $O_2$ supply 19. With this device, an early addition system was compared to a constant flow system for three flow rates (0, 150, and 300 ml/min) at inspired oxygen concentrations equivalent to altitudes of sea level, 1300, 2700, 4500, and 6600 meters (4200, 9000, 14,700, and 21,700 feet). Arterial saturation of hemoglobin was measured to determine which system most efficiently reduced hypoxia. The prior art device of FIG. 5 doubled the $O_2$ delivery efficiency. This device used a cross-sectional area reducer 12 to allow pure oxygen to enter the lungs at the beginning of inspiration (see FIG. 5), but this method also allowed some air to be inhaled at the same time thereby reducing its efficiency. In addition, cross-sectional area reducer 12 introduced breathing resistance which would limit exercise capability.

Figure 6:
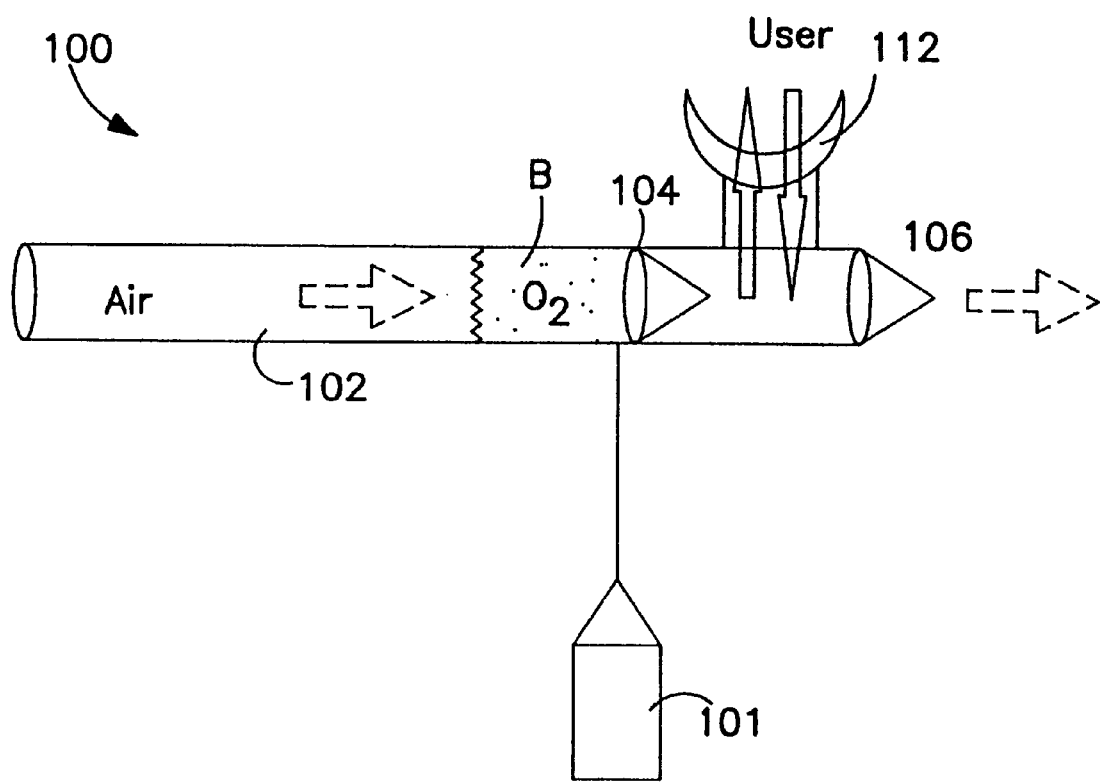
FIG. 6 is a schematic view of applicants' early oxygen addition supplemental oxygen delivery system (EAS)
Figure 7:
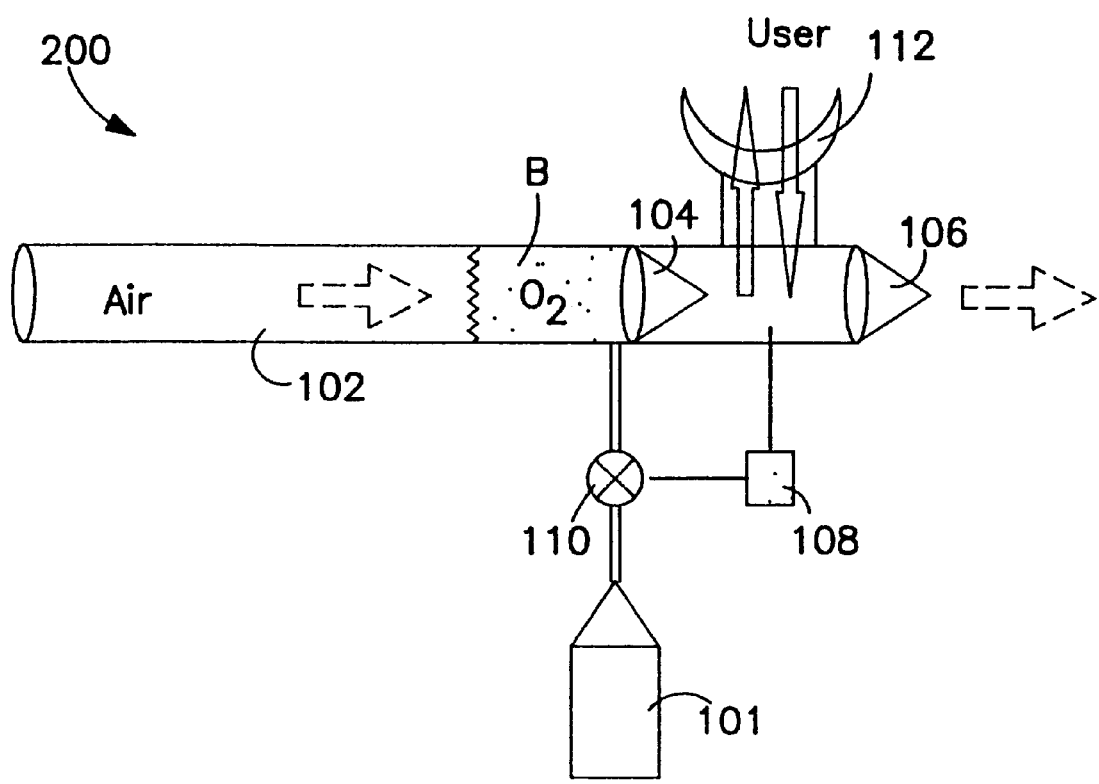
FIG. 7 is a schematic view of applicants' interrupted early oxygen addition supplemental oxygen delivery system (IEAS)

The purpose of applicants' invention is to provide an improved supplemental oxygen delivery system that can be used during exercise at altitude, in emergency first-aid, and for chronically ill patients under normobaric conditions. Applicants will herein describe their novel supplemental oxygen delivery system and then compare their novel system of early oxygen delivery with a control device based on the well known LAERDAL POCKET MASK™ device. Applicants will also describe a further development to the early addition system (EAS) called the partial rebreather that makes $O_2$ delivery even more efficient. The performance of the partial rebreather is compared with the performance of the early addition system. Two closely related embodiments of applicants' invention, generally depicted 100 and 200, are shown in FIGS. 6 and 7 (wherein like parts are designated and by like number) and are best described as the early addition system (EAS) shown in FIG. 6 and the interrupted early addition system (IEAS) shown in FIG. 7. Early addition system 100 allows supplemental oxygen from oxygen source 101 to fill an open-ended reservoir tube 102 during exhalation (see FIG. 6). First and second one-way valves, 104 and 106, allow a bolus B of pure oxygen to be inhaled first, followed by ambient air, thus eliminating the need for the cross-sectional area reducer used in the prior art device of FIG. 5. Since the flow to applicants' device is constant, the size of bolus B depends on the user's breathing frequency.

Oxygen that enters the reservoir during inspiration in the EAS, however, is wasted in the anatomical and device deadspace. The IEAS attempts to reduce this waste by turning off the $O_2$ flow during inspiration (see FIG. 7). This is accomplished with a mouthpiece pressure transducer 108 that senses inspiration and activates a solenoid valve 110 to turn off the $O_2$ flow. Applicants believe that the interrupted early addition system requires the lowest oxygen flow of two embodiments 100 and 200 of applicants' invention and both require significantly less than the LAERDAL POCKET MASK™ CFS device as shown in tests described below.

Figure 8:
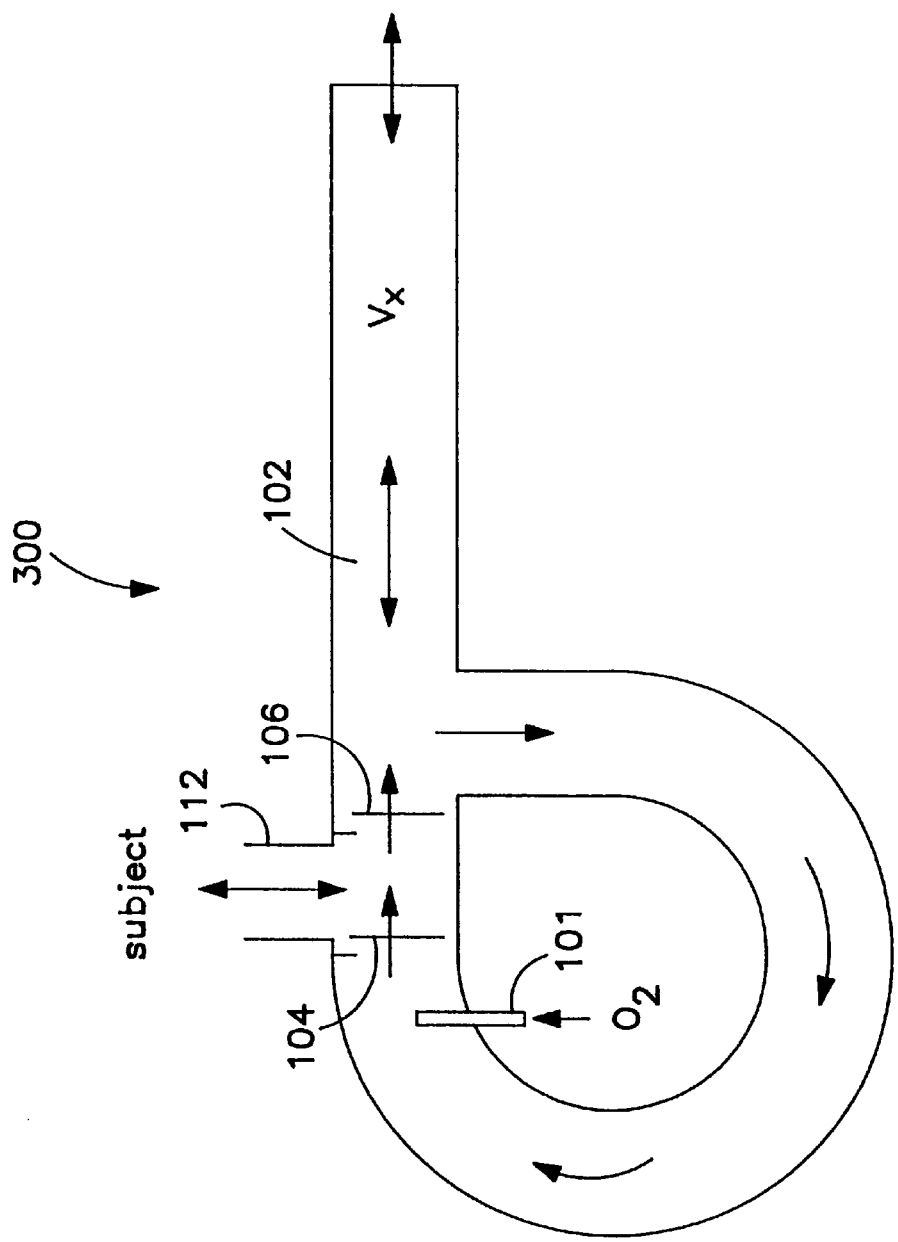
FIG. 8 is a schematic view of applicants' early oxygen addition supplemental oxygen delivery system (EAS) with partial rebreathing capability.

Applicants have also developed a third embodiment 300 of the inventive supplemental oxygen delivery system as depicted by the schematic drawing of FIG. 8. Device 300 provides partial rebreathing capability to either the EAS device 100 or IEAS device 200. Device 300 is constructed and functions as follows: the partial rebreather is based upon the early addition system (EAS) or interrupted early addition system (IEAS). The open-ended $O_2$ reservoir of the EAS and IEAS is connected to its exhalation port to which a deadspace reservoir is added. The volume or length of this deadspace determines the extent to which exhaled gas is rebreathed. The effects of various deadspaces on the efficiency of oxygen use are reported below.

Figure 6A:
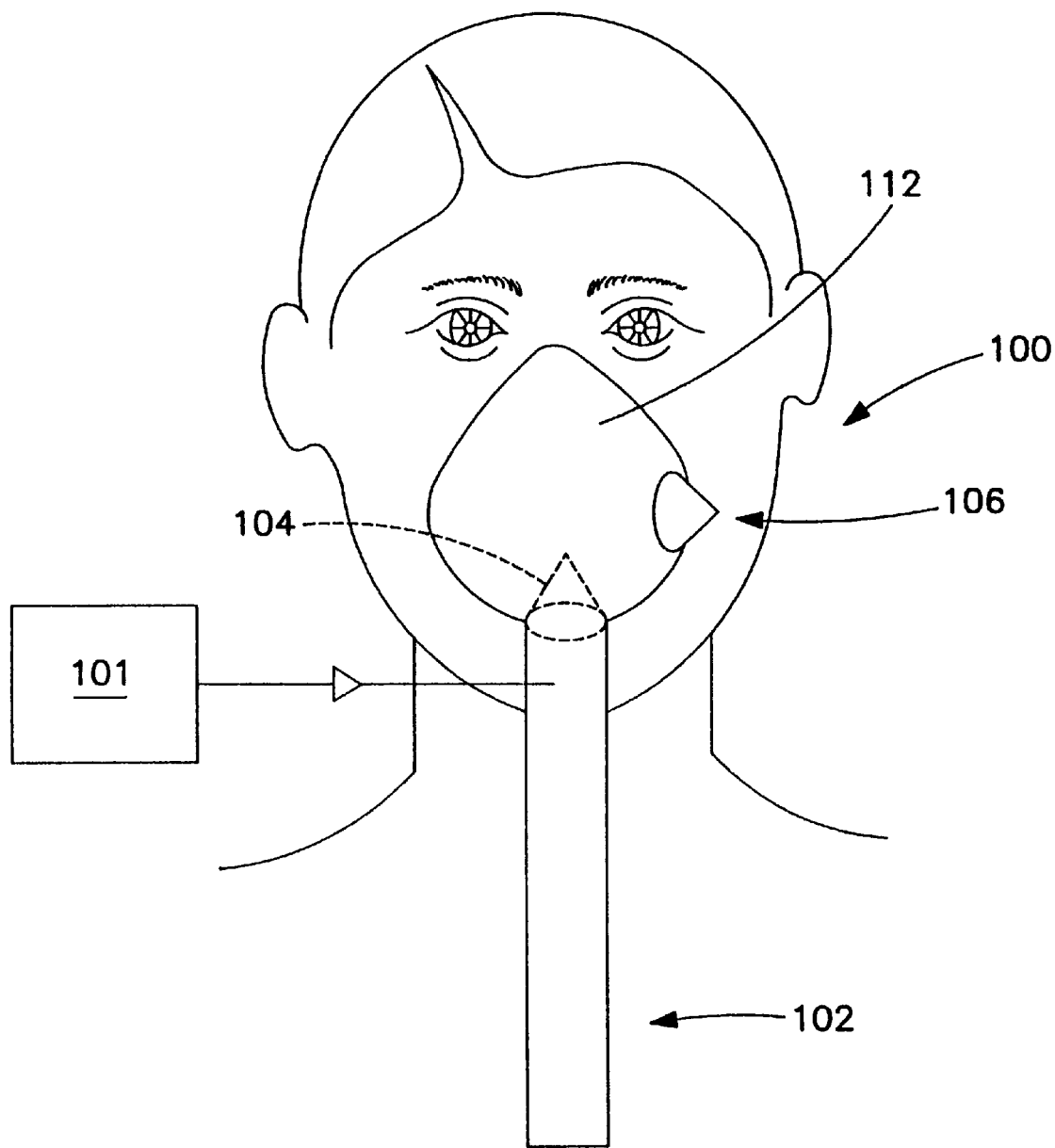
FIG. 6A shows the device of FIG. 6 in the form of an oro-nasal mask.
Figure 7A:
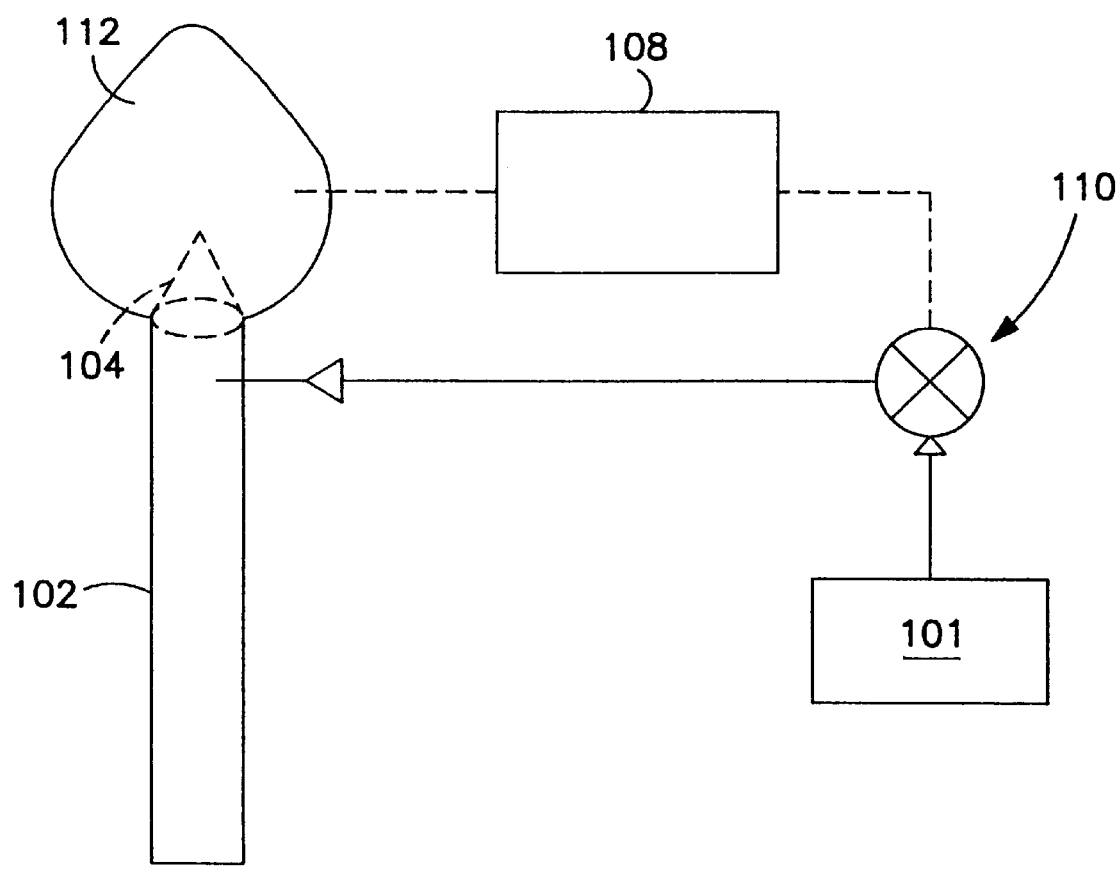
FIG. 7A shows the device of FIG. 7 in the form of an oro-nasal mask.

Applicants wish to note that although embodiments 100 and 200 of applicants' inventive supplemental oxygen delivery system (as well as third embodiment 300 shown in FIG. 8) depict the device as a tube 102 in fluid communication with mouthpiece 112, applicants contemplate that their supplemental oxygen delivery device can be embodied in many different forms that are within the scope of the invention as claimed herein. By way of example, applicants contemplate that the delivery device of the invention can be made in the form of a face mask fitted over the mouth or both the mouth and nose of a patient (oro-nasal mask) as seen in FIGS. 6A, 7A, and 8A of the drawings.

Figure 8B:
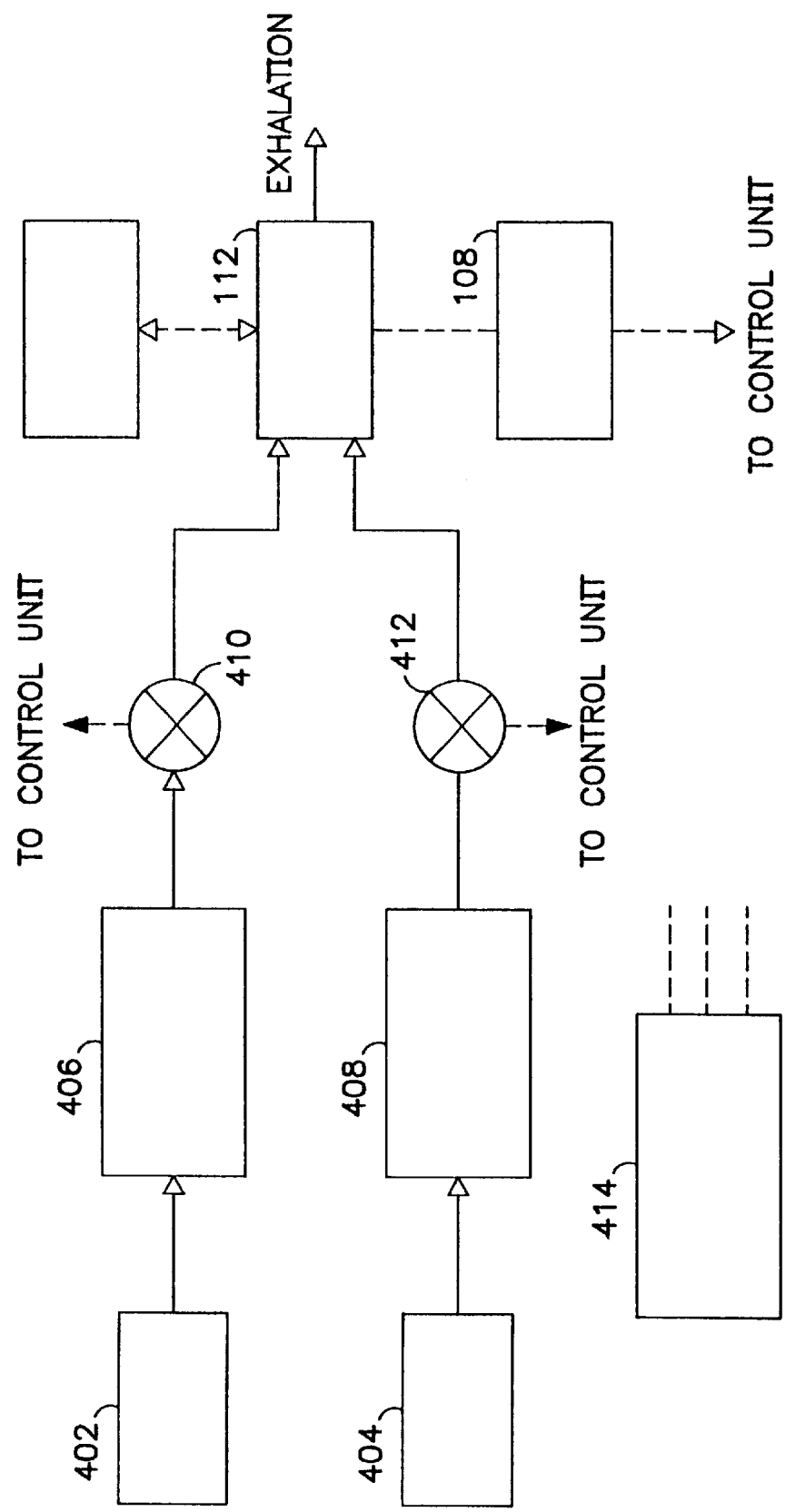
FIG. 8B is a schematic view illustrating the early oxygen addition principle applied to positive pressure breathing.

A further development of the device (see FIG. 8B) applies to positive-pressure breathing that is used in medical emergencies to improve oxygenation of the blood and in high altitude aviation (above 35,000 feet) to cause additional oxygen to dissolve in the blood. Supplies of air and oxygen 402 and 404 respectively, are connected to pressure regulators 406 and 408 respectively, whose outflows are controlled by electronic solenoid valves 410 and 412 respectively. These outflows are in turn connected to an oro-nasal mask 112 worn by a pilot (or patient). A pressure transducer 108 connected to the oro-nasal mask 112 senses the start of inspiration. As the oxygen solenoid valve 412 is normally open, the first part of inspiration will contain 100% oxygen. After a certain time interval that is determined by an electronic control unit 414, the normally open oxygen solenoid valve 412 is closed, and the normally closed air solenoid valve 410 is opened. This allows the latter part of the breath (which fills the deadspace) to be comprised of air. The electronic control unit 414 determines the timing of the solenoid valve operation according to a fixed schedule or adaptive to the breathing frequency.

A. Experimental Testing Protocol

Figure 1:
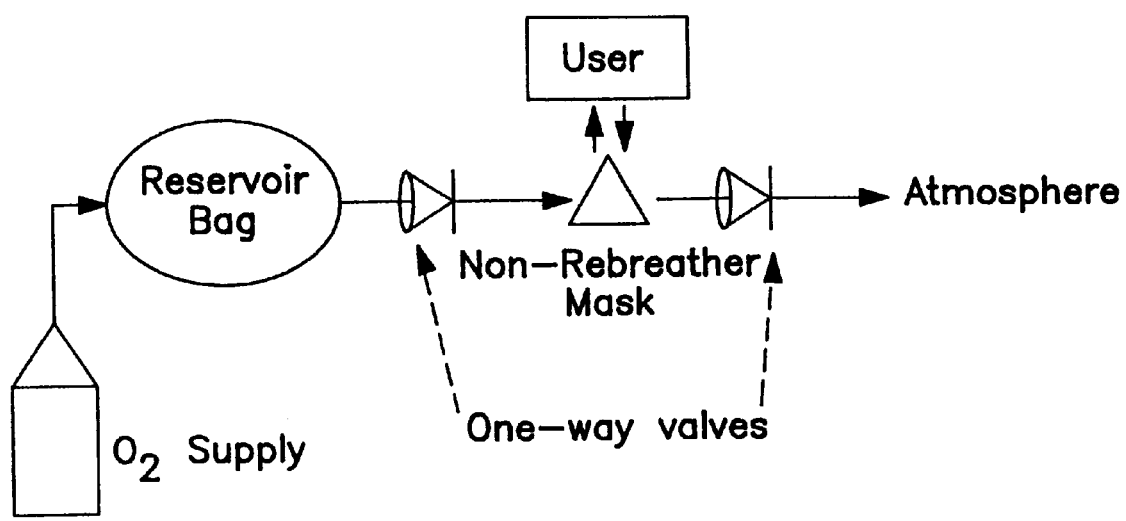
FIG. 1 is a schematic view of a prior art supplemental oxygen system comprising a non-rebreathing mask with attached reservoir bag.
Figure 2:
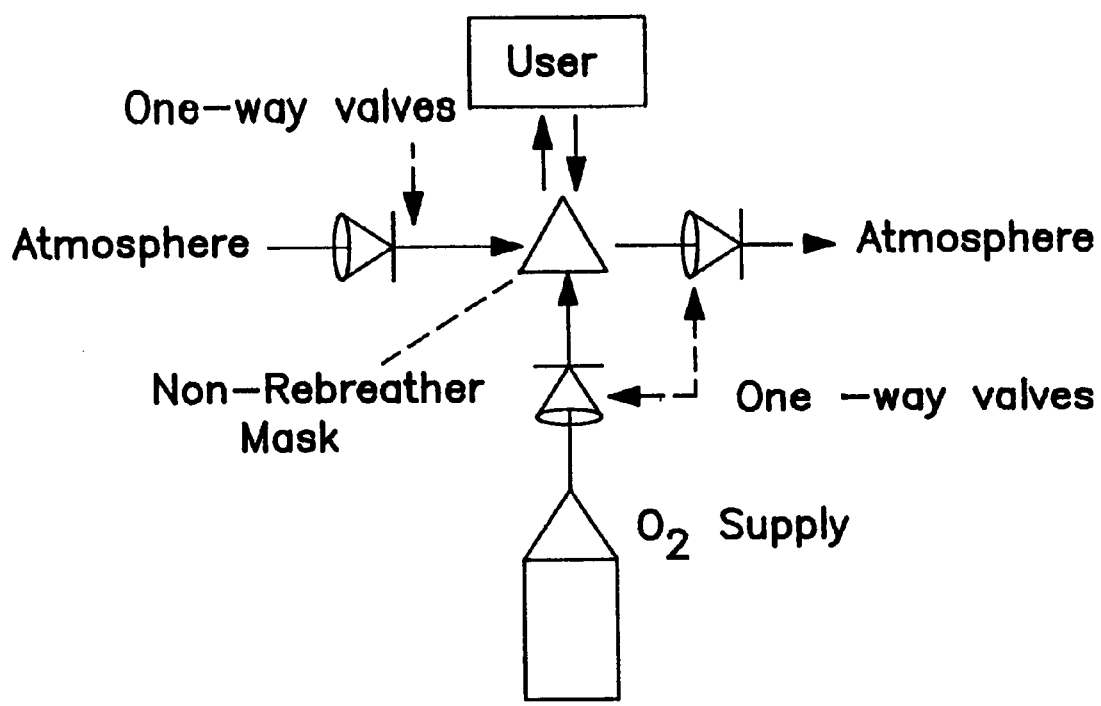
FIG. 2 is a schematic view of a prior art supplemental oxygen system comprising a non-rebreathing mask without a reservoir bag.
Figure 3:
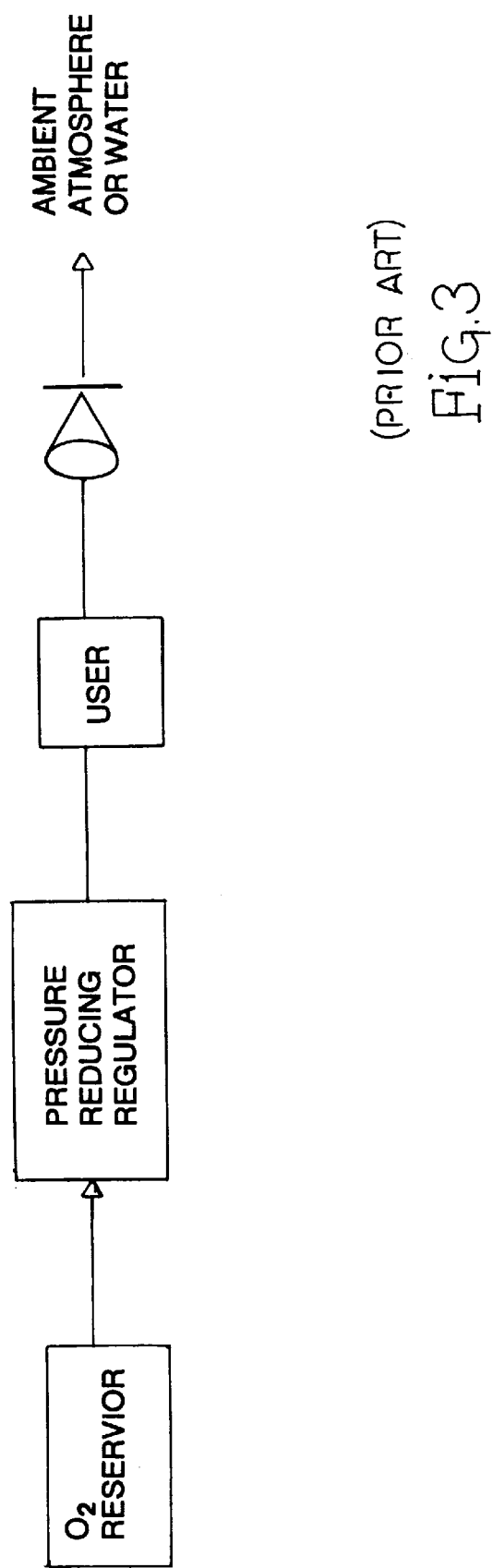
FIG. 3 is a schematic view of an open circuit prior art supplemental oxygen delivery system such as shown in FIG. 1 and FIG. 2.
Figure 4:
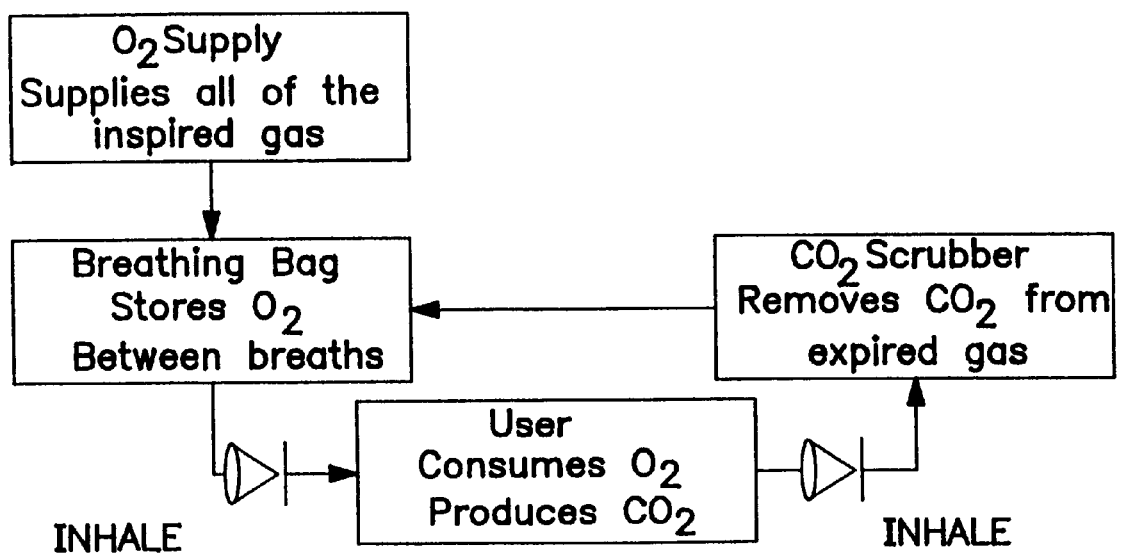
FIG. 4 is a schematic drawing of a closed circuit prior art supplemental oxygen delivery system.
Figure 9:
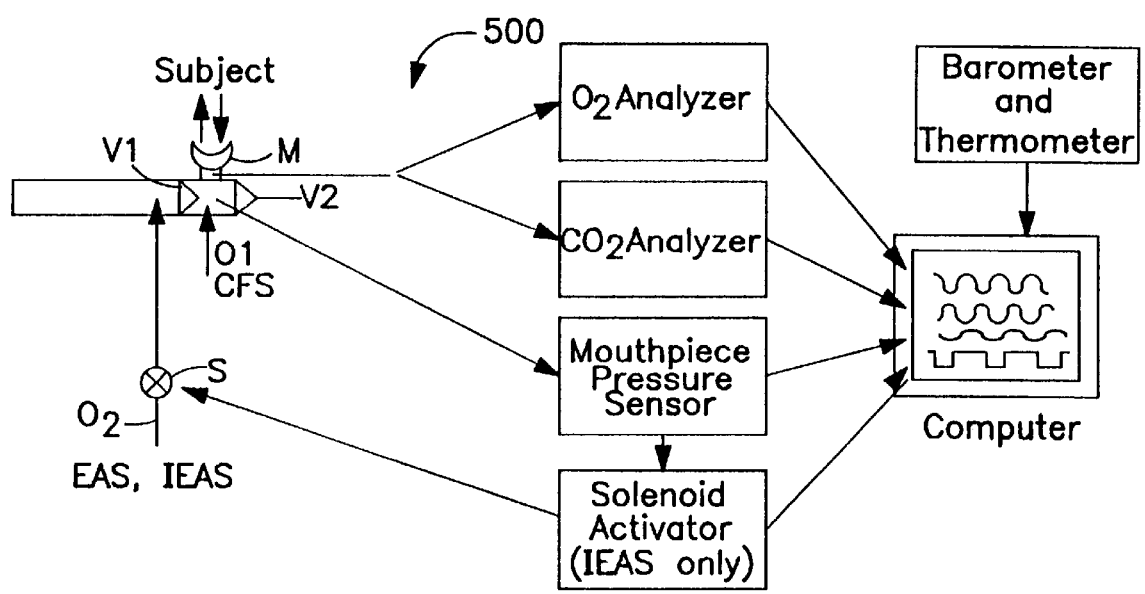
FIG. 9 is a schematic view of applicants' experimental testing device for testing applicants' invention as shown in FIGS. 6 and 7 against a prior art continuous flow system (CFS) supplemental oxygen delivery system.

To compare applicants' two early oxygen delivery devices (EAS and IEAS) 100 and 200 with a constant flow system (CFS) control, a breathing apparatus 500 was constructed that could be easily converted to any of the three systems (see FIG. 9). In this manner, all three systems could be tested on a subject in one sitting. The experimental apparatus used a mouthpiece M instead of an oro-nasal mask to eliminate variability due to air leaks from poor mask fit. Mouthpiece M was a Hans-Rudolph Inc. Model 2700 with 2 one-way non-rebreathing valves V1, V2. The deadspace volume of the mouthpiece was 103 ml. The control system was based on the LAERDAL POCKET MASKυ which is designated as the constant flow system (CFS) and shown in FIG. 2. For the CFS, $O_2$ supply line O1 was connected directly to a port in the center of mouthpiece M (see FIG. 8). When the subject inhaled, oxygen flowed from the supply while air entered mouthpiece M through one-way inhale valve V1. Exhaled gas and unused $O_2$ was exhausted through one-way exhale valve V2 to the atmosphere.

To convert the conventional CFS to applicants' early addition system (EAS) in the testing apparatus, the $O_2$ supply line O1 was moved to a port just in front of one-way inhale valve VI (see FIG. 9). When the subject exhaled, the inhale valve V1 remained shut, and $O_2$ filled the open-ended reservoir tube. The reservoir tube was 204 cm long, 2.0 cm in diameter, and had a volume of 1.44 liters. This was approximately three times larger than normal tidal volume. During inhalation, inhale valve V1 opened, and $O_2$ entered mouthpiece M followed by air. Since the $O_2$ flowed continuously during inhalation, the air inhaled during the latter part of the breath was mixed with $O_2$. As exhalation began, inhale valve V1 closed, exhaled gas exited exhale valve V2, and the cycle repeated.

Applicants' interrupted early addition system (IEAS) was identical to the EAS except for an electrically driven solenoid valve S between the $O_2$ supply line $O_2$ and the device (see FIG. 9). The solenoid was triggered by a mouthpiece pressure transducer. Valve V2 opened during exhalation to allow $O_2$ to fill the reservoir and closed during inhalation to avoid adding oxygen to the latter part of inspiration during which oxygen would be trapped and wasted in the anatomical and apparatus deadspace.

1. Recording Data

Oxygen and carbon dioxide samples were taken from inside mouthpiece M (see FIG. 9) via 1.5 mm diameter microtubing (see FIG. 9). A port on top of the mouthpiece was used as the inlet for supplementary $O_2$ in the CFS and as the mouthpiece pressure sensor of the two test systems. Mouthpiece pressure was not measured for the constant flow system due to interference from the supplemental $O_2$ flow. The oxygen percentage in the gas was measured by an Applied Electronics, Inc. Model No. S-3A $O_2$ analyzer, and the partial pressure of $CO_2$ was measured by a Novametrix Medical Systems, Inc. CAPNOGARD analyzer. The mouthpiece and oxygen supply pressure were measured by Validyne Engineering Corp. pressure transducers. The flow from the $O_2$ supply was converted to standard temperature and pressure, dry (STPD, 0 degrees Celsius, 760 mmHg) as a basis for comparison of the three systems. The $O_2$ flow from the tank was controlled with an Allied Healthcare Products, Inc. flow regulator and valve having preset flow rates. A MACINTOSH computer with MACLAB™ accessory (Chart version 3.3 software) recorded and stored data and displayed it graphically in strip chart form. These data included $O_2$ percentage, CO partial pressure, and mouthpiece pressure as function of time with comments added to document the experimental conditions.

2. Testing Subjects

The experimental protocol was approved by the Duke University Medical Center in Durham, North Carolina. Subjects were unpaid volunteers. Nine subjects were tested on the constant flow system (CFS), early addition system (EAS), and interrupted early addition system (IEAS). Six subjects were tested on a partial rebreather system (PRS) that used four volumes of deadspace.

3. Experimental Test Plan

Each of the nine subjects tested all three systems sequentially. The experiments were scheduled according to subject and equipment availability, and the test order was CFS, EAS, and IEAS for all subjects except one where the order was reversed. The test duration for each device was about 25 minutes followed by a 5 minute break. Tests of all three devices required approximately 90 minutes.

Seven flow rates were tested on each device: 0, 0.5, 1, 2, 4, 6, and 10 liters per minute. The zero flow rate served as a control and allowed the subject's normal fraction of end-tidal $O_2$ to be measured.

The partial rebreather was tested in the same manner as the CFS, EAS, and IEAS. Six subjects tested the partial rebreather with four volumes of added deadspace (0, 0.5, 1.0, and 1.5 liters). Each deadspace was tested with $O_2$ flows of 1, 2, 4, 6, and 10 liters per minute. The effects of the added deadspace on the end-tidal oxygen fraction ($F_{etO2}$) were compared with zero liters of added deadspace which was equivalent to the early addition system (EAS).

4. Procedure

The MACLABTm data acquisition program was set to record at 100 samples per second. All the required channels for the analyzers were turned on and calibrated as described herein. Atmospheric pressure was recorded using a Setra Systems, Inc. digital pressure gauge and entered into a data file. Subjects were given a short brief on the objective of the experiment and how the data would be collected. They were asked to avoid unnecessary sighing, yawning, and other movements that could alter anatomical deadspace and breathing frequency. Subjects were allowed to read during the experiments. The data collection began when the subject put in the mouthpiece and noseclips and began breathing. The first flow to be tested was 0 lpm, and after 3 to 4 minutes, the flow was adjusted to the next higher level. For each different flow, a mark was made on the chart indicating the time and flow. After all seven flows were tested on a particular system, the subject removed the mouthpiece and was given a 5 minute break. During this time, the system was converted into the next system to be tested. This procedure was repeated for the EAS and IEAS. At the end of the experiment, the data was saved to a permanent file, and the apparatus was washed in a 10% Clorox solution and rinsed in water. A similar procedure was followed for testing the partial rebreather system (PRS).

B. Testing Results

Figure 10:
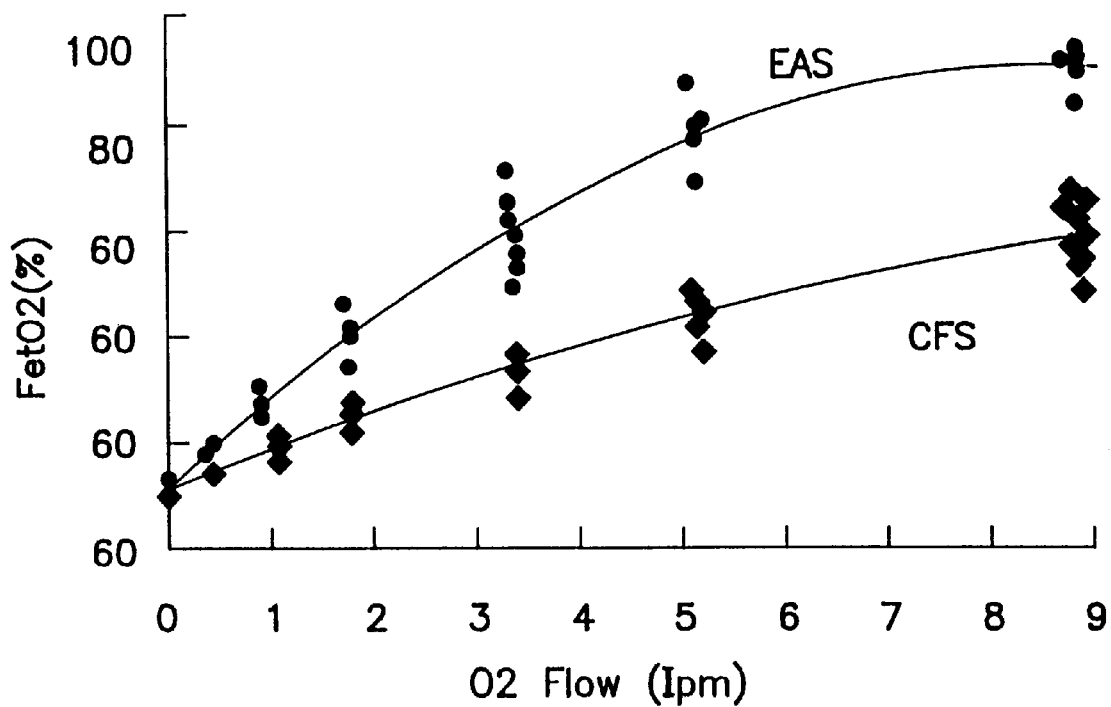
FIG. 10 is a graph illustrating the relationship between oxygen flow and $F_{etO2}$ for the CFS and EAS delivery systems.
Figure 11:
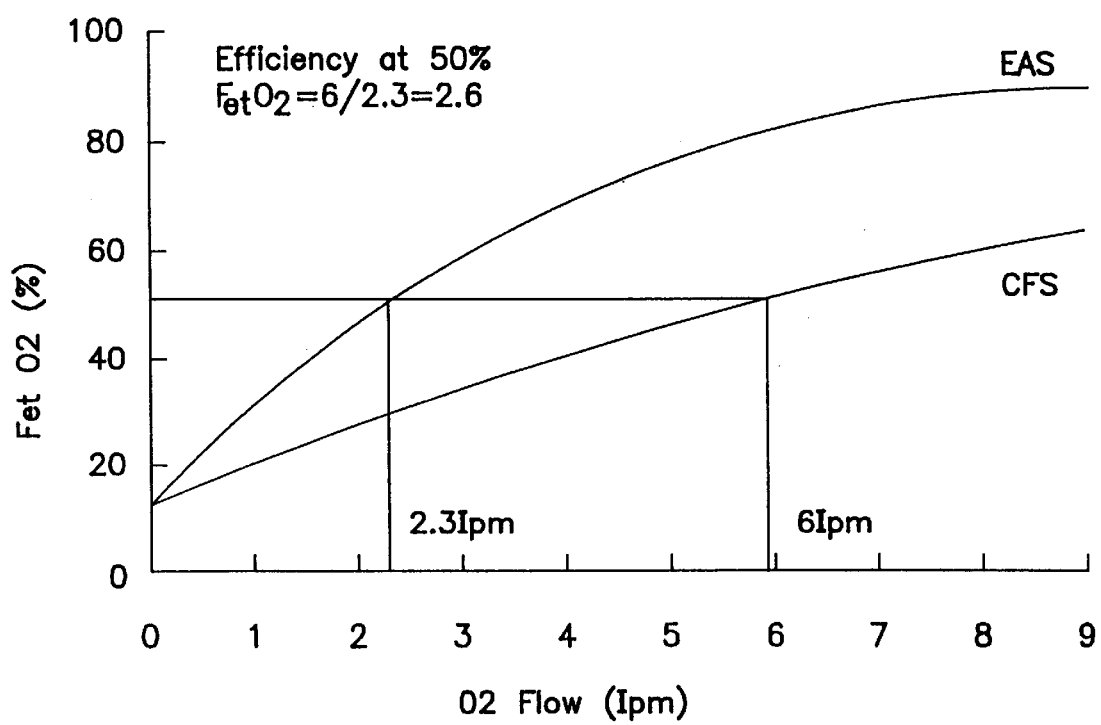
FIG. 11 is a graph illustrating the efficiency of oxygen use by the EAS and CFS delivery systems.

The experimental results from the testing of the CFS, EAS, and IEAS devices were analyzed by multiple linear regression. A similar analysis was applied to the results of the partial rebreather system. The effects of flowrate, device (CFS, EAS, IEAS), deadspace, and subject were all determined to have statistically significant effects on the end-tidal oxygen fraction ($F_{etO2}$). To characterize the performance of each device, a statistical model was computed for the "average" subject. FIG. 10 shows the experimental data and average subject models describing the relationships between the oxygen flow and $F_{etO2}$ for the CFS and EAS devices. FIG. 11 shows that the CFS device requires an $O_2$ flow that is 2.6 times greater than the flow required by the EAS device at $F_{etO2}$=50%, indicating that an oxygen supply would last 2.6 times longer for the EAS device than for the CFS device while providing a $F_{etO2}$ of 50%. This represents an oxygen use efficiency of 260% for the EAS device relative to the CFS device.

Figure 12:
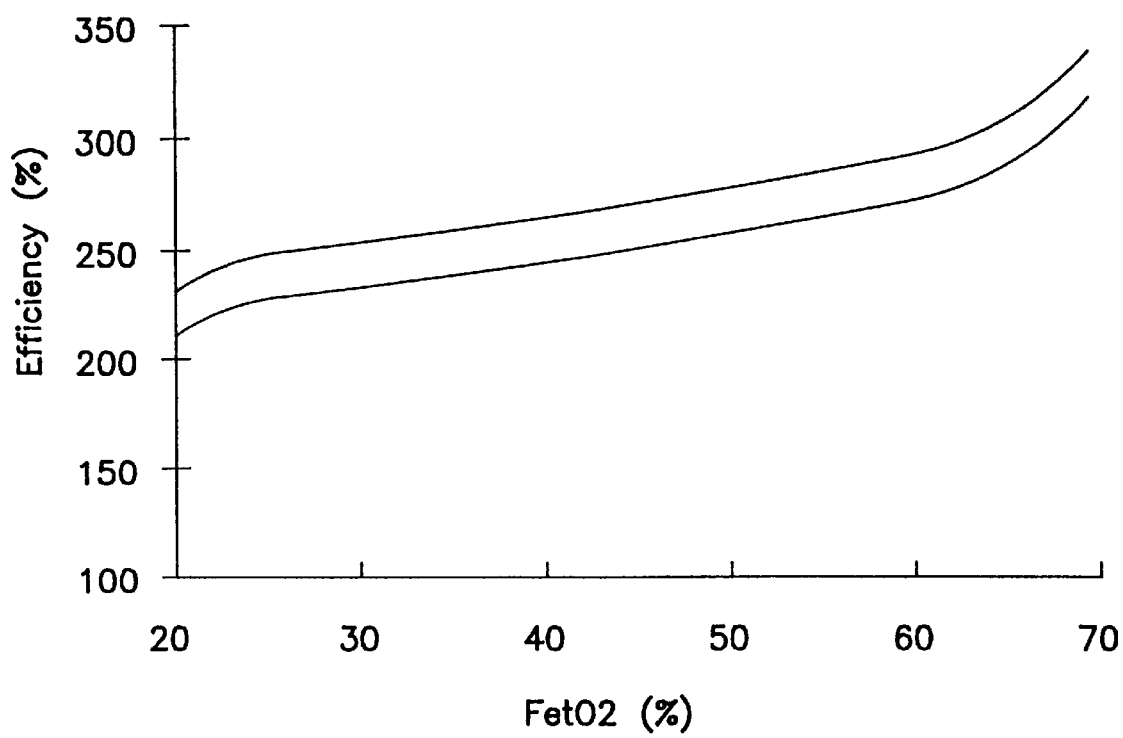
FIG. 12 is a graph illustrating the relationship between oxygen use and $F_{etO2}$ for EAS and IEAS delivery systems relative to CFS delivery systems.

FIG. 12 illustrates how the oxygen use efficiency changes with the $F_{etO2}$ for both the EAS and IEAS devices relative to the CFS device. The EAS device is approximately 2.5 times as efficient (250%) as the CFS device while the IEAS device is approximately 2.7 times as efficient (270%) as the CFS device.

Figure 13:
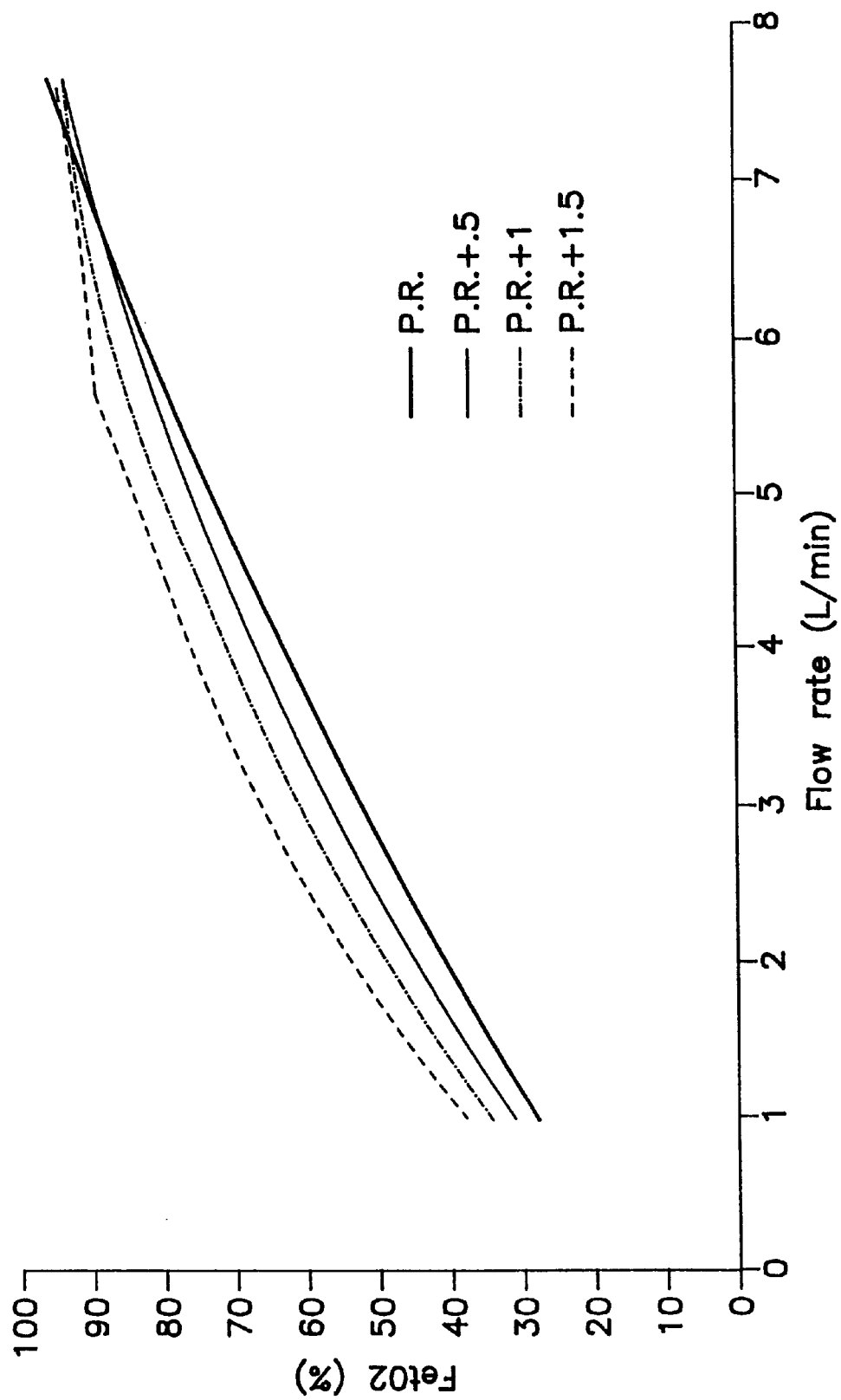
FIG. 13 is a graph illustrating the relationship between oxygen flow and $F_{etO2}$ for the partial rebreather system (PRS) with deadspaces of 0.0, 0.5, 1.0 and 1.5 liters.

FIG. 13 shows the experimental data and average subject models describing the relationship between oxygen flow and $F_{etO2}$ for the partial rebreather system (PRS) with deadspace of 0, 0.5, 1.0, and 1.5 liters. With zero deadspace, the PRS is functionally equivalent to the EAS. As the deadspace increases, a given $F_{etO2}$ is achieved at a lower oxygen flow.

Applicants have developed three embodiments of the invention and two were compared with a constant flow control device to determine the optimal system for delivering a given percentage of oxygen at the lowest supplementary oxygen flow rate. The CFS control device was based on the widely-used LAERDAL POCKET MASK™ which provided a constant flow rate of oxygen. All three devices were tested and both embodiments of applicants' early addition devices used significantly less oxygen to achieve a given oxygen percentage than the CFS device. The IEAS embodiment of applicants' invention was more efficient than the EAS embodiment with the difference being significant at flow rates between 1.2–6.8 lpm.

Oxygen flow rates (lpm) required to achieve inspired oxygen percentages of 50% (for use in treatment of chronically ill patients) and 90% (for use in emergency applications) were determined to be as follows:

|  | CFS | EAS | IEAS |
|---|---|---|---|
| Treatment of Chronic Illness (50%) | 4.6 | 2.9 | 1.7 |
| Use in Emergency Applications (90%) | >10 | 5.7 | 5.3 |

Thus, applicants' devices were approximately 250% more efficient than the control device and would therefore last 2.5 times as long with the same supply of oxygen.

It will be understood that various details of the invention may be changed without departing from the scope of the invention. Furthermore, the foregoing description is for the purpose of illustration only, and not for the purpose of limitation—the invention being defined by the claims.

What is claimed is:

1. A breath-synchronized supplemental oxygen delivery device comprising:

(a) a breathing element for transferring an intake fluid including ambient air and supplemental oxygen to a patient for inhalation by the patient and for transferring an exhaled fluid from the patient;

(b) a reservoir having a reservoir body and an open end, the open end in fluid communication with the atmosphere and the reservoir body in fluid communication with the breathing element;

(c) a non-return inhalation valve disposed within the reservoir body upstream of the breathing element;

(d) a non-return exhalation valve disposed downstream of the breathing element;

(e) an oxygen supply source disposed in fluid communication with the reservoir at a location upstream of the inhalation valve; and (f) supplemental oxygen delivery means cooperatively defined by the inhalation valve, the reservoir and the oxygen supply source for passively developing, during an exhalation effort by the patient, an oxygen bolus upstream of the inhalation valve for delivery to the patient during a first period of an inhalation effort by the patient and for subsequently delivering ambient air to the patient.

2. The breath-synchronized supplemental oxygen delivery device of claim 1, wherein said breathing element comprises a face mask.

3. The breath-synchronized supplemental oxygen delivery device of claim 1, wherein said breathing element comprises a mouthpiece.

4. The breath-synchronized supplemental oxygen delivery device of claim 1, comprising an air exhalation port in fluid communication with the exhalation valve.

5. The breath-synchronized supplemental oxygen delivery device of claim 1, wherein said oxygen supply source is connected to said reservoir by a flexible conduit.

6. The breath-synchronized supplemental oxygen delivery device of claim 1, wherein said reservoir includes a deadspace portion having a first end fluidly communicating with the atmosphere at a location of said reservoir downstream of said exhalation valve and a second end fluidly communicating with said inhalation valve.

7. The breath-synchronized supplemental oxygen delivery device of claim 1, wherein interruption means is provided between said oxygen supply source and said inhalation valve for stopping oxygen flow from said oxygen supply source substantially when said inhalation valve is opened by the inhalation effort.

8. The breath-synchronized supplemental oxygen delivery device of claim 7, wherein said interruption means comprises a pressure transducer and a solenoid valve.

9. A breath-synchronized supplemental oxygen delivery device comprising:
   (a) a face mask for transferring an intake fluid including ambient air and supplemental oxygen to a patient for inhalation by the patient and for transferring an exhaled fluid from the patient;
   (b) a reservoir having a reservoir body and an open end, the open end in fluid communication with the atmosphere and the reservoir body in fluid communication with the face mask;
   (c) a non-return inhalation valve disposed within the reservoir body upstream of the face mask;
   (d) a non-return exhalation valve disposed downstream of the face mask;
   (e) an oxygen supply source disposed in fluid communication with the reservoir at a location upstream of the inhalation valve; and
   (f) supplemental oxygen delivery means cooperatively defined by the inhalation valve, the reservoir and the oxygen supply source for passively developing, during an exhalation effort by the patient, an oxygen bolus upstream of the inhalation valve for delivery to the patient during a first period of an inhalation effort by the patient and for subsequently delivering ambient air to the patient.

10. The breath-synchronized supplemental oxygen delivery device of claim 9, wherein said oxygen supply source is connected to said reservoir by a flexible conduit.

11. The breath-synchronized supplemental oxygen delivery device of claim 9, wherein said reservoir includes a deadspace portion having a first end fluidly communicating with the atmosphere at a location of said reservoir downstream of said exhalation valve and a second end fluidly communicating with said inhalation valve.

12. The breath-synchronized supplemental oxygen delivery device of claim 9, wherein interruption means is provided between said oxygen supply source and said inhalation valve for stopping oxygen flow from said oxygen supply source substantially when said inhalation valve is opened by the inhalation effort.

13. The breath-synchronized supplemental oxygen delivery device of claim 12, wherein said interruption means comprises a pressure transducer and a solenoid valve.

14. A breath-synchronized supplemental oxygen delivery device comprising:
   (a) a mouthpiece for transferring an intake fluid including ambient air and supplemental oxygen to a patient for inhalation by the patient and for transferring an exhaled fluid from the patient;
   (b) a reservoir having a reservoir body and an open end, the open end in fluid communication with the atmosphere and the reservoir body in fluid communication with the mouthpiece;
   (c) a non-return inhalation valve disposed within the reservoir body upstream of the mouthpiece;
   (d) a non-return exhalation valve disposed downstream of the mouthpiece;
   (e) an oxygen supply source disposed in fluid communication with the reservoir at a location upstream of the inhalation valve; and
   (f) supplemental oxygen delivery means cooperatively defined by the inhalation valve, the reservoir and the oxygen supply source for passively developing, during an exhalation effort by the patient, an oxygen bolus upstream of the inhalation valve for delivery to the patient during a first period of an inhalation effort by the patient and for subsequently delivering ambient air to the patient.

15. The breath-synchronized supplemental oxygen delivery device of claim 14, wherein said oxygen supply source is connected to said reservoir by a flexible conduit.

16. The breath-synchronized supplemental oxygen delivery device of claim 14, wherein said reservoir includes a deadspace portion having a first end fluidly communicating with the atmosphere at a location of said reservoir downstream of said exhalation valve and a second end fluidly communicating with said inhalation valve.

17. The breath-synchronized supplemental oxygen delivery device of claim 14, wherein interruption means is provided between said oxygen supply source and said inhalation valve for stopping oxygen flow from said oxygen supply source substantially when said inhalation valve is opened by the inhalation effort.

18. The breath-synchronized supplemental oxygen delivery device of claim 14, wherein said interruption means comprises a pressure transducer and a solenoid valve.

19. A method for administration of supplemental oxygen comprising the steps of:
   (a) applying a breathing element to the face of a patient to transfer an intake fluid including ambient air and supplemental oxygen to the patient for inhalation by the patient and to transfer an exhaled fluid from the patient;
   (b) providing a reservoir having a reservoir body and an open end, whereby the open end fluidly communicates with the atmosphere and the reservoir body fluidly communicates with the breathing element inspiration port and air expiration port, respectively;
   (c) providing a non-return inhalation valve in the reservoir body upstream of the breathing element to permit the intake fluid to flow from the reservoir to the breathing element;
   (d) providing a non-return exhalation valve downstream of the breathing element to permit the exhaled fluid to flow from the breathing element, whereby an inhalation effort by the patient opens the inhalation valve and closes the exhalation valve, and whereby an exhalation effort by the patient closes the inhalation valve and opens the exhalation valve;
   (e) introducing a stream of oxygen into the reservoir from an oxygen supply source at a point upstream of the inhalation valve
   (f) during the exhalation effort, causing an oxygen bolus to develop upstream of the inhalation valve;
   (g) during a first period of the inhalation effort, delivering the oxygen bolus to the patient, and
   (h) during a subsequent period of the inhalation effort, delivering ambient air to the patient.

20. The method according to claim 19, including recirculating a portion of the exhaled fluid to an upstream side of the inhalation valve.

21. The method according to claim 19, including interrupting the stream of oxygen from the oxygen supply source when the inhalation valve is opened by the inhalation effort.

22. The method of claim 21, including providing a pressure transducer and solenoid valve to interrupt the stream of oxygen from the oxygen supply source.

23. A breath-synchronized supplemental oxygen device comprising:
  (a) breathing means for transferring a gaseous fluid including ambient air and supplemental oxygen to and from a patient;
  (b) a reservoir in fluid communication with the atmosphere and with the breathing means;
  (c) a non-return inhalation valve disposed within the reservoir upstream of the breathing means;
  (d) a non-return exhalation valve disposed within the reservoir downstream of the breathing means;
  (e) an oxygen supply source disposed in fluid communication with the reservoir at a location upstream of the non-return inhalation valve; and
  (f) means cooperatively defined by the non-return inhalation valve, the reservoir and the oxygen supply source for developing a mass of oxygen upstream of the non-return inhalation valve for delivery to the patient during a first period of the patient's inhalation effort and for delivering a subsequent mass of ambient air.

* * * * *